United States Patent
Baillet et al.

(10) Patent No.: US 9,724,713 B2
(45) Date of Patent: Aug. 8, 2017

(54) FLUID OR POWDERY PRODUCT DISPENSING DEVICE

(71) Applicant: APTAR FRANCE SAS, Le Neubourg (FR)

(72) Inventors: Matthieu Baillet, Bonsecours (FR); Francois Le Maner, La Valle Montaure (FR); Franck Poullain, La Haye Malherbe (FR); Holger Kehrer, Bois Guillaume (FR)

(73) Assignee: APTAR FRANCE SAS, Le Neubourg (FR)

( * ) Notice: Subject to any disclaimer, the term of this patent is extended or adjusted under 35 U.S.C. 154(b) by 0 days.

(21) Appl. No.: 14/902,733

(22) PCT Filed: Jul. 4, 2014

(86) PCT No.: PCT/FR2014/051738
§ 371 (c)(1),
(2) Date: Jan. 4, 2016

(87) PCT Pub. No.: WO2015/001281
PCT Pub. Date: Jan. 8, 2015

(65) Prior Publication Data
US 2016/0296957 A1    Oct. 13, 2016

(30) Foreign Application Priority Data

Jul. 5, 2013  (FR) ..................... 13 56667

(51) Int. Cl.
| B05B 11/06 | (2006.01) |
| A61M 11/02 | (2006.01) |
| A61M 15/00 | (2006.01) |

(52) U.S. Cl.
CPC .......... B05B 11/062 (2013.01); A61M 11/02 (2013.01); A61M 15/0028 (2013.01);
(Continued)

(58) Field of Classification Search
CPC ... B05B 11/06; B05B 11/062; B05B 11/3001; B05B 11/3023; B05B 11/3039;
(Continued)

(56) References Cited

U.S. PATENT DOCUMENTS

| 4,017,007 A | 4/1977 | Riccio |
| 5,328,099 A | 7/1994 | Petit et al. |

(Continued)

FOREIGN PATENT DOCUMENTS

| EP | 0 575 239 A1 | 12/1993 |
| FR | 2 186 853 A6 | 1/1974 |

(Continued)

OTHER PUBLICATIONS

International Search Report of PCT/FR2014/051738 dated Sep. 18, 2014.

(Continued)

*Primary Examiner* — Darren W Gorman
(74) *Attorney, Agent, or Firm* — Sughrue Mion, PLLC (57) ABSTRACT

A dispenser device, including an outlet, air expeller including a piston that slides in an air chamber between rest position and dispensing positions, and a reservoir containing a dose composition. The reservoir includes an air inlet connected to the air expeller, and a composition outlet connected to the outlet, the air inlet including a composition retainer member, and the composition outlet being closed by a closure element force fitted in the composition outlet of the reservoir. A mechanical opening system co-operates with the closure element to expel it from its closed position while the device is actuated. The piston, when in its rest position, co-operates in non-airtight manner with the air chamber so that the air chamber communicates with the atmosphere. The piston includes an inner lip co-operating with a cylindrical surface, the cylindrical surface including fluting co-operat- (Continued)

ing in non-airtight manner with the inner lip in the rest position.

3 Claims, 12 Drawing Sheets

(52) U.S. Cl.
CPC .......... *A61M 15/0061* (2014.02); *B05B 11/06* (2013.01); *A61M 2202/04* (2013.01); *A61M 2202/064* (2013.01); *A61M 2205/073* (2013.01); *A61M 2205/583* (2013.01); *A61M 2205/584* (2013.01)

(58) Field of Classification Search
CPC .. A61M 11/02; A61M 11/006; A61M 11/007; A61M 15/0028; A61M 15/0061; A61M 2202/04; A61M 2202/064; A61M 2205/073; A61M 2205/583; A61M 2205/584
See application file for complete search history.

(56) References Cited

U.S. PATENT DOCUMENTS

| | | | |
|---|---|---|---|
| 5,511,698 A * | 4/1996 | Solignac | B05B 11/007 141/2 |
| 6,398,074 B1 | 6/2002 | Bruna et al. | |
| 6,866,039 B1 * | 3/2005 | Wright | A61M 15/0041 128/203.15 |
| 6,877,672 B2 * | 4/2005 | Stihl | A61M 15/0028 222/82 |
| 8,056,762 B2 * | 11/2011 | Wright | A61M 15/0028 222/209 |
| 2004/0050885 A1 | 3/2004 | Stradella | |
| 2007/0129665 A1 * | 6/2007 | Dickens | A61M 15/0028 604/26 |
| 2012/0325861 A1 | 12/2012 | Pardonge | |

FOREIGN PATENT DOCUMENTS

| | | |
|---|---|---|
| FR | 2 775 963 A1 | 9/1999 |
| FR | 2 780 388 A1 | 12/1999 |
| FR | 2 956 649 A1 | 8/2011 |
| WO | 91/12895 A1 | 9/1991 |
| WO | 99/46055 A1 | 9/1999 |
| WO | 02/45866 A1 | 6/2002 |

OTHER PUBLICATIONS

International Preliminary Report on Patentability dated Jan. 14, 2016 from the International Bureau in counterpart application No. PCT/FR2014/051738.

* cited by examiner

FLUID OR POWDERY PRODUCT DISPENSING DEVICE

CROSS REFERENCE TO RELATED APPLICATIONS

This is a National Stage of International Application No. PCT/FR2014/051738 filed Jul. 4, 2014, claiming priority based on French Patent Application No. 1 356 667 filed Jul. 5, 2013, the contents of all of which are incorporated herein by reference in their entirety.

FIELD OF INVENTION

The present invention relates to a dispenser device for dispensing a fluid or powder composition, and more particularly it relates to a device for dispensing a dose of a composition contained in a reservoir, by means of a flow of air under pressure.

BACKGROUND

Document WO 99/46055 discloses such a device in which a spherical closure element, which closes the outlet of the reservoir, is expelled by the flow of air created by an air expeller. In order to use a dispenser device more particularly for dispensing powder, the air pressure necessary for actuating the device must be sufficiently high to guarantee that the dose is dispensed completely, and that it is broken up, if that is necessary. In the above-mentioned device, the air pressure necessary to actuate the device is determined by the resistance opposed by the ball in order to be expelled. That resistance is relatively difficult to control and to predetermine since it depends on the friction between the ball and its cylindrical seat in which it is engaged for the purpose of closing said reservoir in leaktight manner. Consequently, it may be necessary to minimize the interference between the sphere and its cylindrical seat, and obviously that might spoil the effectiveness of the closure. Furthermore, it may be necessary to minimize the depth and the positioning of the sphere in its seat so as to make it easier to expel. It may also be necessary to provide air pressure that is relatively high, which is not always easy to achieve by means of a pump system or of a bellows system, in particular when the air expellers are actuated manually by the patient. Furthermore, dispensing, i.e. expelling the ball from its seat, may take place at different positions along the stroke of the pump or of the bellows of the air expeller, such that the precise moment of dispensing the composition cannot always be predetermined in exact manner. Finally, there is a limit on the materials that can be chosen for the sphere and for its seat.

Document WO 02/45866 describes a device in which a closure ball is expelled mechanically by a rod that is secured to an air expeller. That embodiment presents several drawbacks. Thus, an air expeller that is airtight in any position may, in particular during transport or storage, present a risk of said air expeller being triggered in unwanted manner in the event of there being a difference in pressure between the inside and the outside of the air expeller. Furthermore, the device in document WO 02/45866 is not reusable, and the entire device must be thrown away after it has been used. In particular, for ecological and economic reasons, it may be desirable to have a reusable device in which the reservoir is changed after each actuation, but not the air expeller.

Document FR 2 186 853 describes another prior-art device.

Certain Objects and Advantages of Embodiments of the Invention

An object of the present invention is to provide a fluid or powder dispenser device that does not have the above-mentioned drawbacks.

An object of the present invention is thus to provide a fluid or powder dispenser device that is simple and inexpensive to manufacture and to assemble.

Another object of the present invention is to provide such a fluid or powder dispenser device that makes it possible to use an air expeller that is very simple, inexpensive, and reliable, and that does not require the creation of a particularly powerful flow of air.

An object of the present invention is to provide such a fluid or powder dispenser device that can be used a plurality of times with a plurality of different reservoirs.

Another object of the present invention is to provide a fluid or powder dispenser device in which the closure element acts, on every occasion, to guarantee leaktight closure of the reservoir at rest.

The present invention thus provides a dispenser device for dispensing a fluid or powder composition, the dispenser device including: a dispenser outlet; an air expeller for generating a flow of air while the device is being actuated, said air expeller including a piston that slides in an air chamber between a rest position and a dispensing position, said air chamber including a cylindrical body in which said piston slides in airtight manner; and at least one reservoir that contains a single dose of composition, said reservoir including an air inlet that is connected to said air expeller, and a composition outlet that is connected to said dispenser outlet, said air inlet including a composition retainer member for retaining the composition in the reservoir until the composition is dispensed, and said composition outlet being closed by a closure element that is force fitted in the composition outlet of the reservoir; said device further including a mechanical opening system that co-operates with said closure element so as to expel it mechanically from its closed position while the device is being actuated, said piston of said air expeller, when in its rest position, co-operating in non-airtight manner with said air chamber, in such a manner that said air chamber is in communication with the atmosphere in the rest position, said piston including an inner lip that is suitable for co-operating with a cylindrical surface, said cylindrical surface including fluting that co-operates in non-airtight manner with said inner lip of the piston in its rest position.

Advantageously, said cylindrical surface is secured to a first rod portion that slides in said air chamber during actuation, said piston co-operating in airtight manner with said cylindrical body in any position, and co-operating in non-airtight manner with said cylindrical surface only in the rest position.

Advantageously, said reservoir is mounted in removable manner on said air expeller, such that after the device has been actuated, the empty reservoir may be removed from said air expeller and replaced by a new full reservoir, said air expeller being suitable for returning into its rest position so as to enable said new full reservoir to be actuated.

BRIEF DESCRIPTION OF THE DRAWINGS

These characteristics and advantages, and others, appear more clearly from the following detailed description of several embodiments, given by way of non-limiting example, and with reference to the accompanying drawings, in which.

DESCRIPTION OF NON-LIMITING EMBODIMENTS OF THE INVENTION

In its various above-described variants and embodiments, the present invention relates more particularly to a device of the type disclosed in document WO 02/45866. That document describes the general operation of the device.

However, it should be understood that the present invention is not limited to that type of device, but, on the contrary, applies to any type of fluid and powder dispenser device that includes a reservoir closed by a closure element, the contents of the reservoir needing to be expelled by a flow of air.

Figure 1:
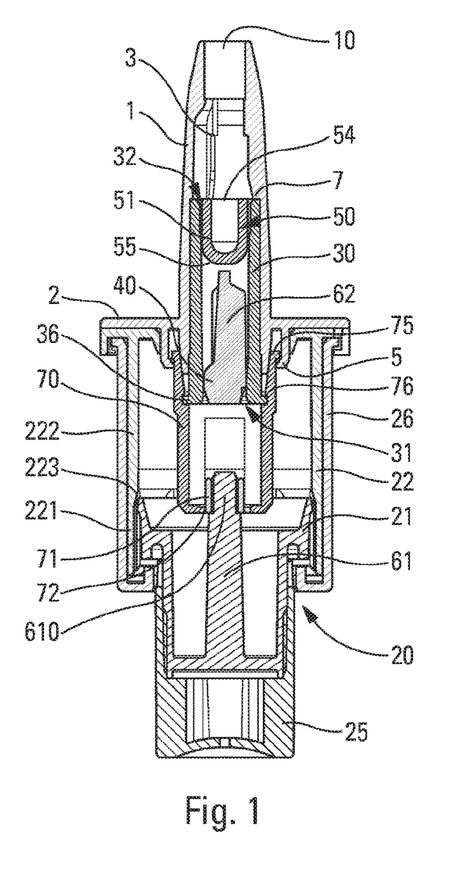
FIG. 1 is a diagrammatic section view of a fluid or powder dispenser device in a first embodiment, in its rest position.

It is understood that throughout the description, the terms "top", "bottom", "upwards", and "downwards" refer to the upright position of the device shown in particular in FIG. 1.

FIGS. 1 to 14 show a first advantageous embodiment.

The device includes a reservoir 30 including an air inlet 31 and a composition outlet 32. The air inlet 31 of the reservoir is connected to an air expeller 20, and the composition outlet 32 of the reservoir is connected to a dispenser outlet 10 of the device. The composition outlet 32 is closed by a closure element 50 that is force fitted in said composition outlet 32. The air inlet 31 is provided with a composition retainer member 40 that is suitable for retaining the composition in the reservoir before the device is actuated. The air expeller 20 is actuated manually by the user, and is suitable for creating a flow of air that passes through the reservoir 30 so as to deliver the composition that it contains towards the dispenser outlet 10.

Figure 10:
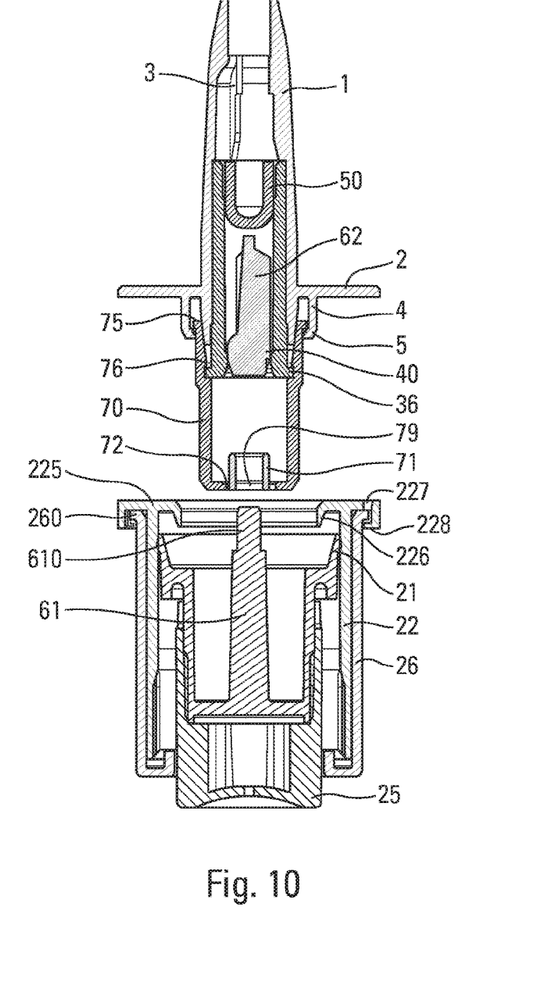
FIG. 10 is a view similar to the view in FIG. 9, showing only the air expeller, after removal of the empty reservoir, together with a new full reservoir, before assembly.

The reservoir 30 is secured, in particular as a tight fit, in a dispenser head 1 that includes the dispenser outlet 10. A radial shoulder 7 of the dispenser head 1 advantageously defines the assembled position of the reservoir 30 in said dispenser head 1. A breakable part 70 is assembled on said reservoir 30 and on said dispenser head 1, thereby forming a unit assembly, as can be seen in FIG. 10. At the air inlet 31, the reservoir includes a radial edge 36 that projects outwards and that is suitable for fastening to said breakable part 70, in particular by snap-fastening in a groove 76 of the breakable part 70. In addition, said breakable part 70 also includes a top axial edge 75 that is fastened to said dispenser head, in particular by snap-fastening on a snap-fastener profile 5 that is formed on the bottom edge of an axial flange 4 of the dispenser head 1. At its bottom axial edge, the breakable part 70 includes a central axial opening 79 in which an indicator element 71 is fastened. The indicator element 71 is connected to said bottom axial edge by at least one breakable bridge 72. Preferably, there are a plurality of breakable bridges 72, e.g. three of them.

The device includes a mechanical opening system 61, 62 that is preferably secured to the air expeller 20, i.e. it is actuated simultaneously with said air expeller 20 being actuated, and that is suitable for co-operating with said closure element 50 so as to expel it mechanically from its closed position while the device is being actuated. In the embodiment shown in the figures, the mechanical opening system includes a set of rods 61, 62, having a first rod portion 61 that is secured to the air expeller 20, and a second rod portion 62 that is thrust by said first rod portion 61 when the device is actuated. At the end of their actuation stroke, i.e. in the dispensing position, the set of rods 61, 62 co-operate with the closure element 50 so as to expel it mechanically from its closed position.

The composition retainer member 40 may advantageously be made integrally with the second rod portion 62. Thus, the composition retainer member 40 can be made in leaktight and airtight manner before the device is actuated, the air pressure created by the air expeller 20 penetrating into the reservoir 30 only when said retainer member 40 is moved together with the second rod portion 62, by being thrust by the first rod portion 61.

Figure 15:
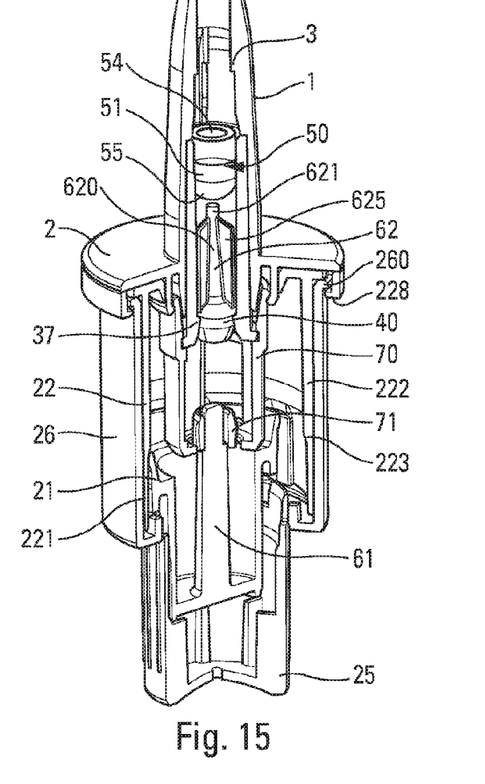
FIG. 15 is a cut-away diagrammatic perspective view showing a fluid or powder dispenser device in a second embodiment, in its rest position.
Figure 16:
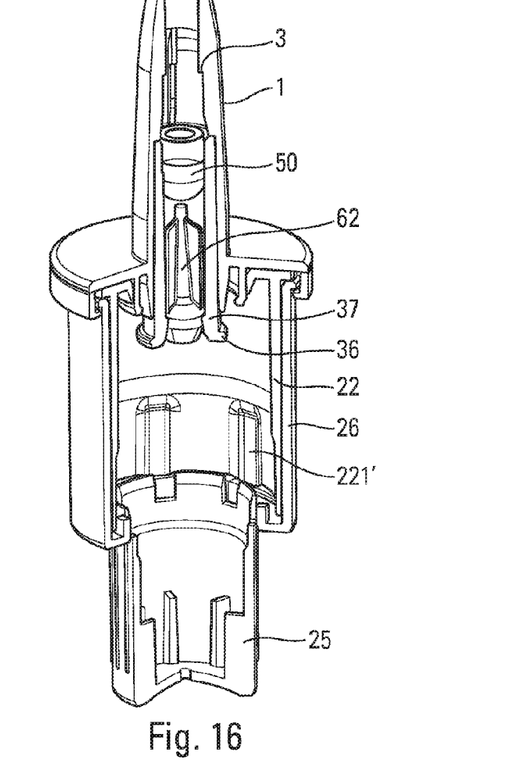
FIG. 16 is a view similar to the view in FIG. 15, more particularly showing the air expeller.

The retainer member 40 is advantageously made in the form of a rigid disk that is extended inside the reservoir by the second rod portion 62. The second rod portion 62 is preferably made with a central portion 620 that may be cone shaped or of a shape that is approximately similar, terminated by a top axial end 621 and a plurality of side fins 625, e.g. three. The fins cannot be seen explicitly in FIGS. 1 to 14, but they can be seen in particular in FIG. 15, which shows, in perspective, the part that forms the retainer member 40 and the second rod portion 62, and that is entirely similar to the part shown in section in particular in FIG. 1. In particular, the fins 625 guide the second rod portion 62 in the reservoir body during actuation. Advantageously, said disk forming the retainer member 40 is force fitted in the reservoir body 30. Preferably, as can be seen in particular in FIGS. 7 and 8, in the proximity of the air inlet 31, the reservoir 30 includes a radial shoulder 37 that defines a bottom reservoir portion of inside diameter that is small. In its storage and rest position, the retainer member 40 is force fitted in the bottom portion of small inside diameter, so as to guarantee sealed (both airtight and leaktight) closure of the reservoir. When the retainer member 40 is moved away from its rest position, it no longer co-operates with the bottom portion of small inside diameter, and thus no longer closes said air inlet 31 of the reservoir in sealed manner. In a variant, said retainer member could be fastened, e.g. heat-sealed, to the reservoir body. The second rod portion 62 includes a top axial end 621 that co-operates with the closure element 50 during actuation.

The closure element 50 may be spherical, e.g. a ball made of plastics material, as shown in FIGS. 19 to 33, or non-spherical, as shown in FIGS. 1 to 16. The closure element 50 may then include a cylindrical portion 51 that co-operates with said composition outlet 32 to define a peripheral sealing surface. Sealing is thus formed not along a sealing line, as with a spherical ball, but over a cylindrical surface. The embodiment shown in FIGS. 1 to 16 shows an advantageous closure element 50 that includes a hollow axial cylindrical sleeve. At one axial end, which is the end facing towards the inside of the reservoir 30 in the closed position, the closure element 50 includes a rounded portion 55, in particular a hemi-spherical portion, so as to make it easier for the composition to pass towards the dispenser outlet 10 during actuation. At the other axial end 54, the hollow sleeve is advantageously open. This embodiment gives a degree of flexibility to the closure element 50, which makes it easier to put it into place and makes it possible, in part, to compensate for manufacturing dimensional tolerances, so as to guarantee leaktight closure in the closed position.

The air expeller shown in FIG. 1 includes a piston 21 that slides in an air chamber 22, the piston 21 being actuated manually by the user. Advantageously, such actuation is performed by means of a pusher element 25 that is assembled on said piston 21.

The piston 21 is secured to the first rod portion 61, advantageously being formed integrally therewith.

Figure 3:
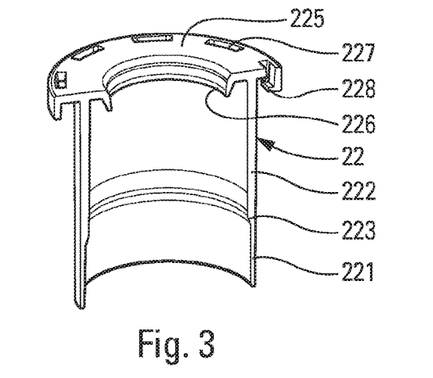
FIG. 3 is a perspective view of a detail of the air chamber of the FIG. 1 device.
Figure 4:
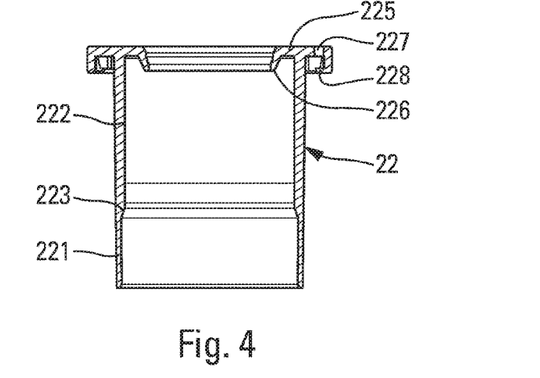
FIG. 4 is a view similar to the view in FIG. 3, in section.

As can be seen more particularly in FIGS. 3 and 4, the air chamber 22 advantageously comprises a cylindrical body 222 that includes a radial flange 225 at its top axial edge. The radial flange 225 firstly extends radially inwards from said cylindrical body 222, where it includes an axial extension 226 that extends axially downwards. The purpose of the axial extension 226 is to co-operate, advantageously in substantially airtight manner, with the outer surface of the axial flange 4 of the dispenser head 1, when the device is assembled. The radial flange 225 secondly extends radially outwards from said cylindrical body 222, where it includes fastener means 228 for fastening to an outer body 26 that is assembled around said air chamber 22. Advantageously, the fastener means comprise one or more snap-fastener profiles 228 that are suitable for snap-fastening on a top radial edge 260 of said outer body 26. Advantageously, in order to simplify manufacture, a plurality of snap-fastener profiles 228 are distributed around the periphery of said radial flange 225, facing corresponding slots 227 that simplify molding the part that forms the air chamber, in particular avoiding having to use complex drawer molds.

In its rest position, as can be seen in FIG. 1, the air expeller 20 is open to the atmosphere. In the embodiment in FIG. 1, the opening to the atmosphere is obtained by a larger-diameter cylindrical portion 221 of the cylindrical body of the air chamber 22. In the larger-diameter cylindrical portion 221 provided at the bottom axial edge of the air chamber 22, the piston 21 of the air expeller 20 does not co-operate in airtight manner with said air chamber. When the device is actuated, the piston 21 moves away from said larger-diameter portion 221 and thus co-operates in airtight manner with a cylindrical body portion 222 of the air chamber 22, thereby compressing the air contained in the air chamber. Advantageously, the transition between the cylindrical body portion 222 and the larger-diameter portion 221 is made progressively, e.g. by a conical wall portion 223, so as to make it easier for the piston to move away from its rest position. At its bottom axial edge, the outer body 26 advantageously includes a radial rim 261 that is turned inwards, and that makes it possible in particular to protect the air expeller 20 in its rest position, in particular the larger-diameter portion 221 of the air chamber 22 and the piston 21.

When the device is assembled, as can be seen in particular in FIG. 1, said indicator element 71 of the breakable part 70 is engaged around a constricted end 610 of the first rod portion 61. The breakable bridges 72 are suitable for breaking while the device is being actuated, as can be seen in FIGS. 1 to 2.

Figure 2:
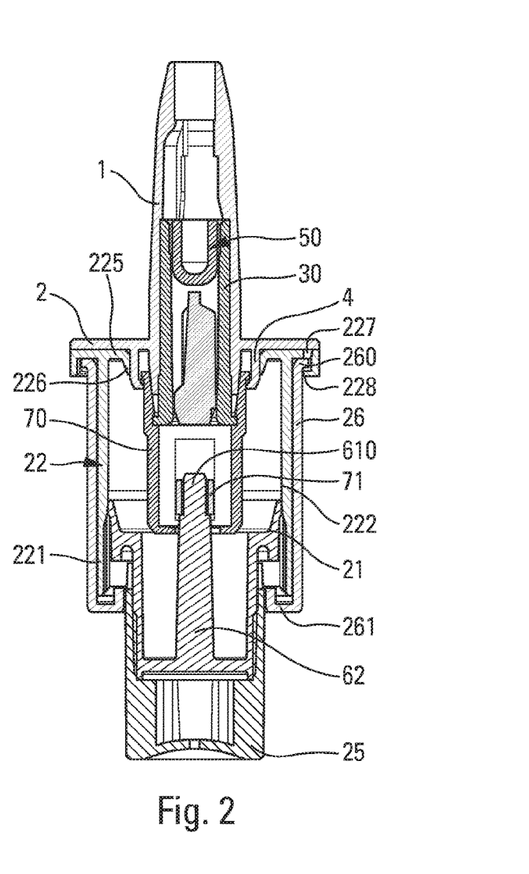
FIGS. 2 and 5 to 8 are views similar to the view in FIG. 1, showing various stages of actuation.

Actuation of the device is shown in FIGS. 2 and 5 to 8. Thus, when it is desired to actuate the device, the user firstly places fingers on the finger rest 2 of the dispenser head 1, and secondly a thumb on the pusher element 25, and exerts an actuation force that initially breaks the breakable bridges 72, then moves the first rod portion 61 and the piston 21 towards the dispensing position. At the beginning of actuation, as can be seen in FIG. 2, the piston 21 of the air expeller co-operates in airtight manner with the air chamber 22, such that the air contained in said air chamber 22 is compressed progressively during actuation.

Figure 5:
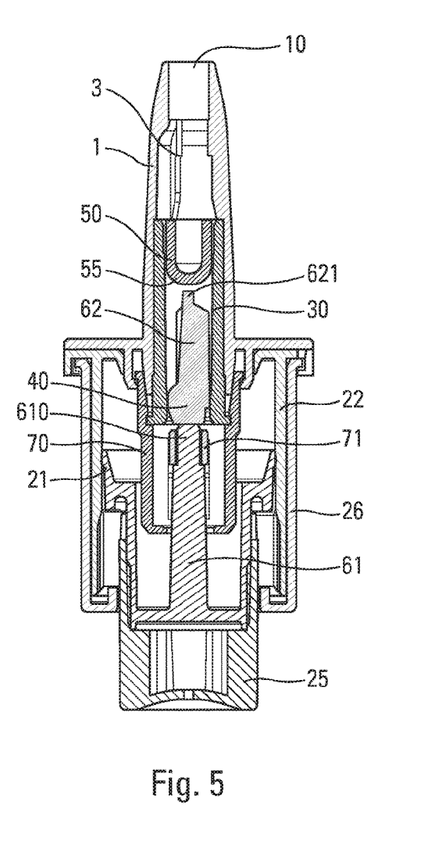

In the position in FIG. 5, the top axial end 610 of the first rod portion comes into contact with the retainer member 40 and thus with the second rod portion 62.

Figure 6:
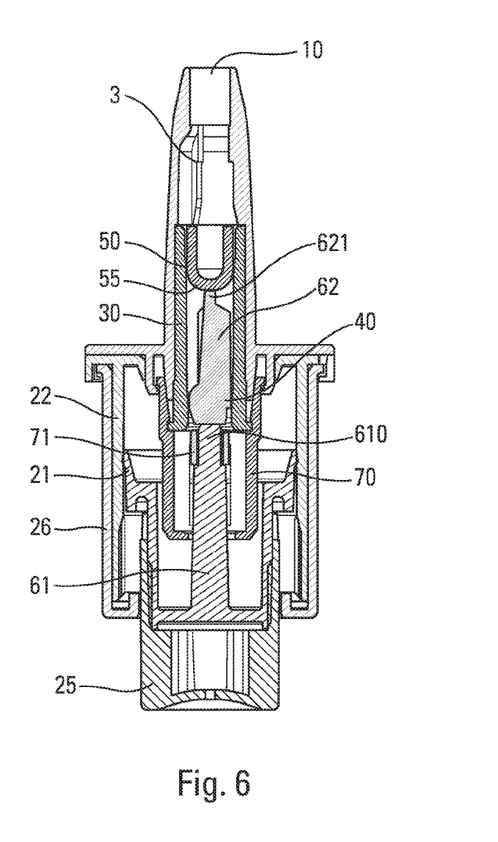

Continued actuation moves said retainer member 40 axially upwards inside the reservoir 30, thus away from its position of sealed shutting or closing of the air inlet, as can be seen in FIG. 6. At that moment, the compressed air in the air chamber 22 can thus penetrate into the reservoir 30. At the same moment, the top axial end 621 of the second rod portion 62 comes into contact with the rounded portion 55 of the closure element 50.

Figure 7:
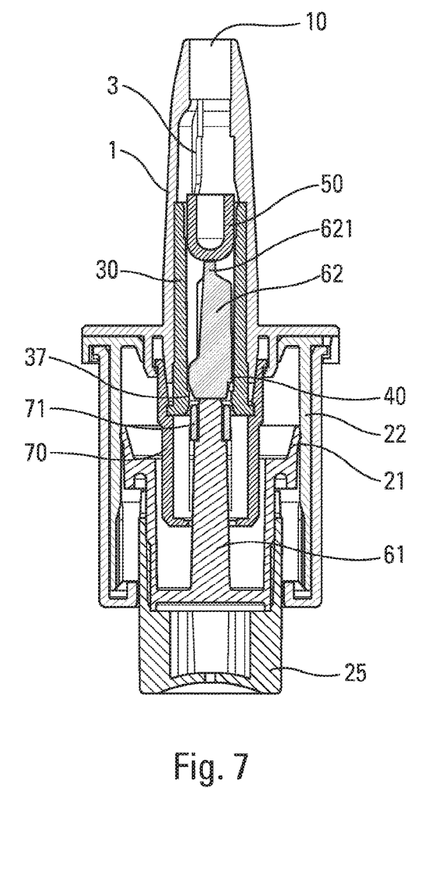

Continued actuation thus moves the closure element 50 axially upwards, away from its closed position, as can be seen in FIG. 7.

Figure 8:
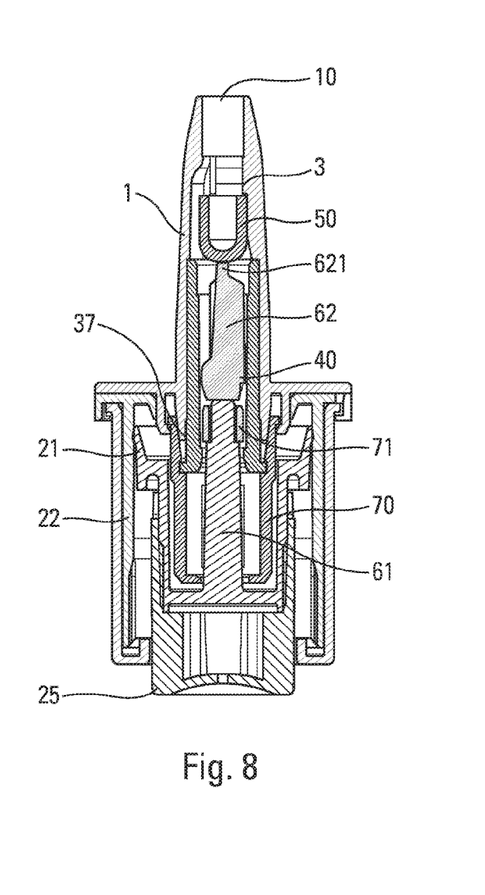
Figure 9:
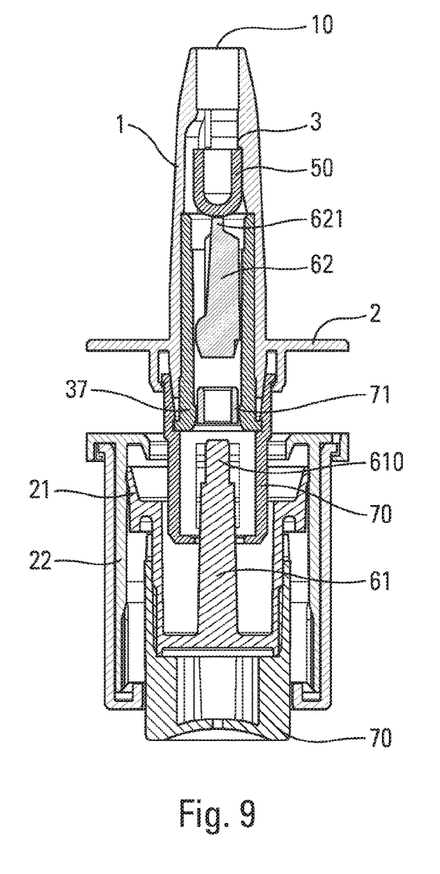
FIG. 9 is a view similar to the view in FIG. 8, showing the removal of the empty reservoir.

When the sealing of the closure element 50 is broken, said closure element is expelled out from the reservoir 30 so as to enable the fluid or powder to be dispensed under the effect of the compressed air. The closure element 50 thus becomes jammed in splines 3 of the dispenser head 1, which splines prevent in particular any risk of said closure element being expelled out from said dispenser head 1. The dispensing position, at the end of the actuation stroke and after dispensing the composition, is shown in FIG. 8.

Figure 11:
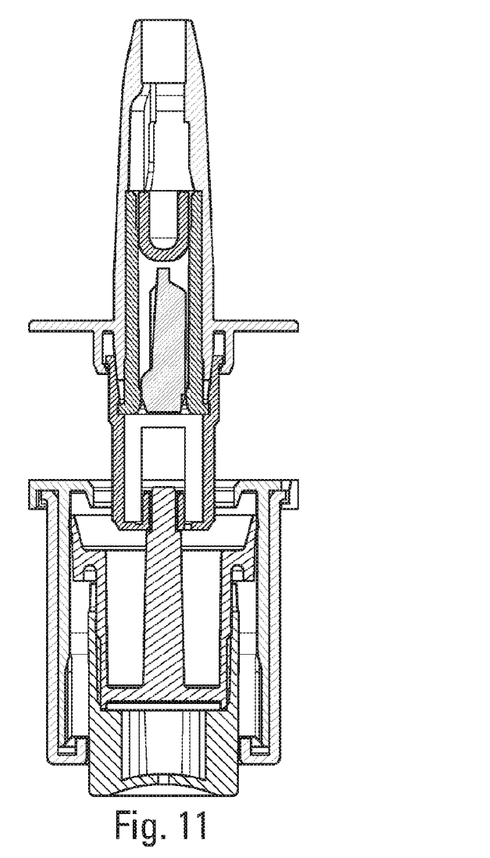
FIGS. 11 and 12 are views similar to the view in FIG. 10, showing the insertion of a new full reservoir.
Figure 12:
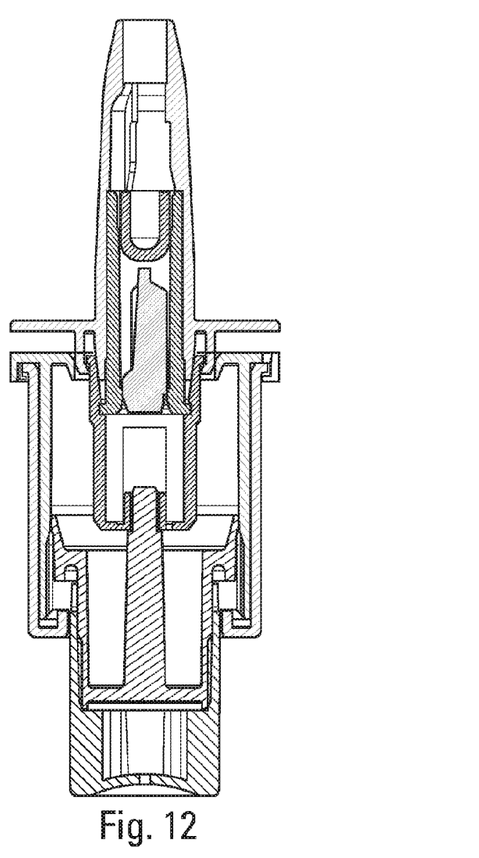
Figure 13:
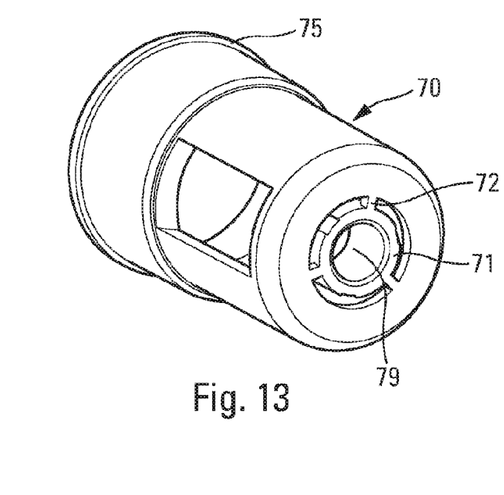
FIG. 13 is a diagrammatic perspective view of the breakable part of the reservoir.
Figure 14:
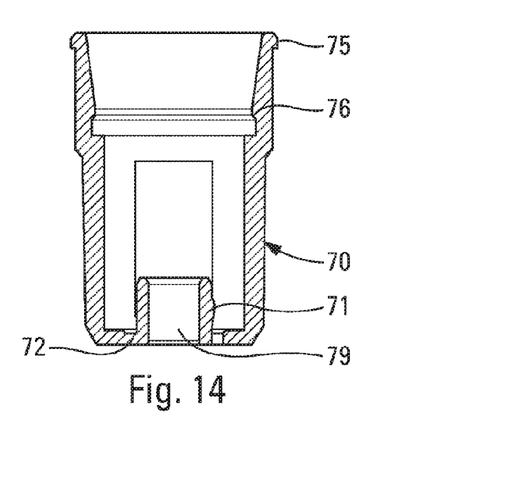
FIG. 14 is a view similar to the view in FIG. 13, in section.

The first embodiment shown in FIGS. 1 to 14 shows a refillable device. Thus, in the dispensing position shown in FIG. 8, the user may remove the assembly formed by the dispenser head 1, the reservoir 30, and the breakable body 70 from the air expeller. The indicator element 71 remains in the reservoir 30, retained in particular by said radial shoulder 37, and the breakable part 70 slides along the first rod portion 61 so as to separate therefrom. After the empty reservoir has been removed, as shown in FIG. 10, a new full reservoir may be assembled on the air expeller. FIG. 11 shows an assembly formed by a dispenser head 1, a reservoir 30, and a breakable part 70 having an indicator element 71 that is positioned around the constricted end 610 of the first rod portion 61. The user thus inserts the new assembly into the air expeller, thus pushing the first rod portion 61 downwards, thereby causing the piston 21 to slide back towards its rest position. To do this, the resistance to the piston 21 returning is less than the resistance necessary for breaking the breakable bridges 72 of the breakable part 70. At the end of insertion, just before arriving in the rest position in FIG. 1, the axial flange 4 of the dispenser head 1 comes to co-operate with the axial extension 226 of the air chamber. The end of insertion then moves the piston 21 towards the larger-diameter portion 221, thus eliminating the sealing at that location, and the air expeller is thus open to the atmosphere in its rest position, as can be seen in FIG. 1. The device is thus ready for a new actuation cycle. The first embodiment is advantageous in that it does not include any metal springs. Furthermore, the indicator element 71 forms a usage indicator that, when it is contained in said reservoir, informs the user that the reservoir has been emptied. The indicator element 71 may thus advantageously be made so as to be easily identifiable, e.g. in a particular color. The presence of the breakable part also provides another advantage in that it protects the reservoir and the retainer member 40 before use, and in particular at the moment when it is inserted in the air expeller.

Figure 17:
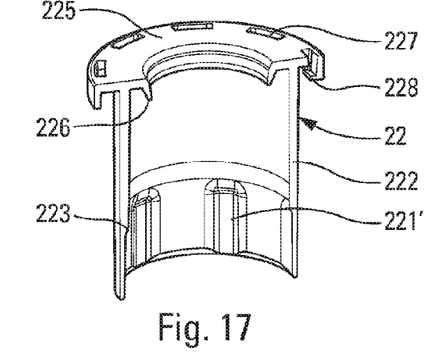
FIG. 17 is a perspective view of a detail of the air chamber of the device in FIGS. 15 and 16.
Figure 18:
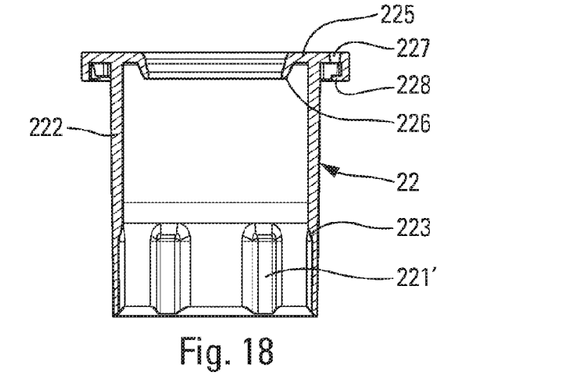
FIG. 18 is a view similar to the view in FIG. 17, in section.

FIGS. 15 to 18 show a second embodiment. The second embodiment is very close to the first embodiment, the only difference being the way in which the air expeller 20 is put into communication with the surrounding air in its rest position, which, in this embodiment, is not achieved by means of a larger-diameter cylindrical portion of the body of the air chamber 22, but via grooves 221' that are formed in the bottom portion of the cylindrical body 222 of the air chamber 22. Thus, instead of being peripheral, as in the embodiment in FIGS. 1 to 14, in this embodiment, in its rest position, the air chamber 22 is put into communication with the atmosphere via air passages that are provided by said grooves 221', which air passages are distributed around the periphery. More particularly, FIGS. 17 and 18 show the grooves 221' with which the piston 21 co-operates in its rest position.

FIGS. 19 to 23 show a third embodiment. This embodiment differs from the first embodiment in FIGS. 1 to 14 in several aspects. Thus, the closure element 50 is spherical, in particular a ball. The second rod portion 62 does not include fins, and the retainer member 40 is extended downwards by an axial extension 43 that comes into contact with the top axial end 610 of the first rod portion 61 during actuation.

In addition, in this embodiment, there is no outer body, but merely a cover 27 that is assembled on the bottom axial edge of the air chamber 22.

The piston 21 is separate from the first rod portion 61, and slides both relative to the air chamber 22 and to a cylindrical surface 614 that is secured to the first rod portion 61.

The air chamber 22 is completely cylindrical, the air chamber 22 in its rest position being put into communication with the surrounding air at the fluting or grooves 615 that are formed in said cylindrical surface 614 and that co-operate with the piston 21, in particular in its rest position. The piston 21 thus includes an inner lip 215 that slides in airtight manner over the cylindrical wall 614 during actuation, and that co-operates with said fluting 615 in its rest position. The piston 21 also includes an axial extension 216 that co-operates with a top edge 251 of the pusher element 25 that moves said piston 21 in the air chamber 22 during actuation.

A spring 80 is provided between the radial flange 225 of the air chamber 22 and the part that forms the first rod portion 61 and the cylindrical surface 614, so as to return the air expeller automatically into its rest position after actuation.

The operating principle is as follows.

Figure 19:
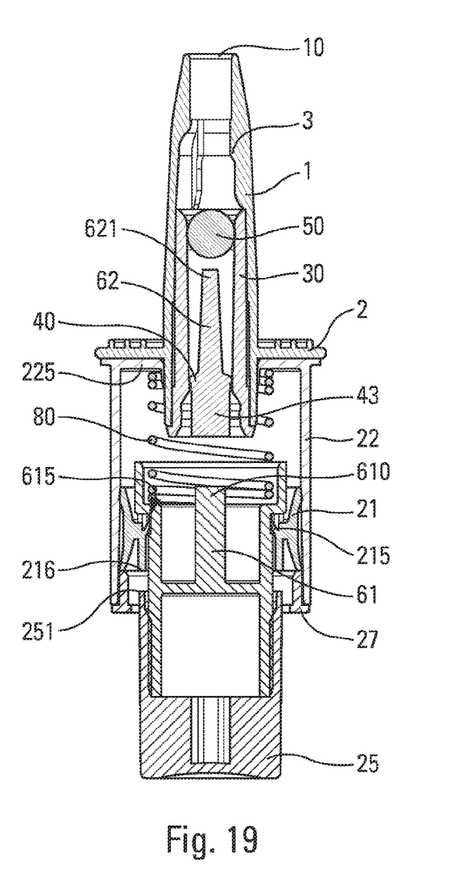
FIGS. 19 to 22 are diagrammatic section views of a third embodiment shown respectively in the rest position, during actuation, in the dispensing position, and during return of the air expeller towards its rest position.
Figure 20:
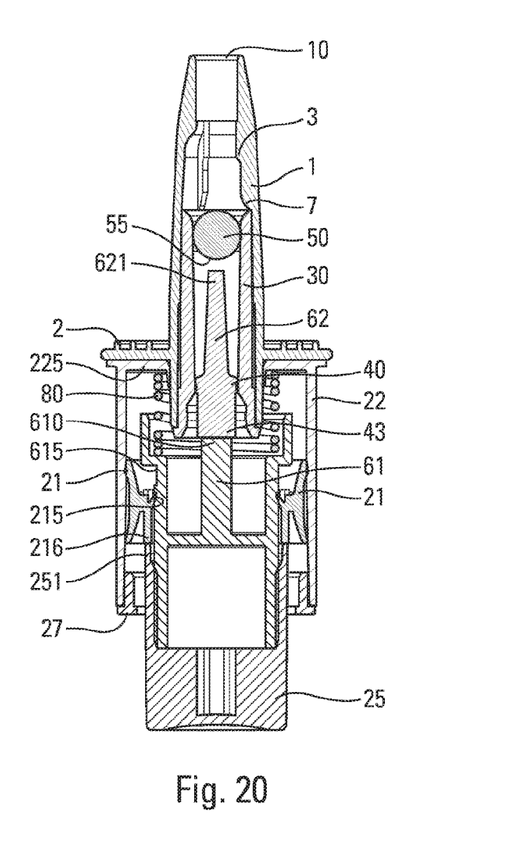

In the rest position in FIG. 19, the reservoir 30 is closed in sealed manner by the retainer member 40 and by the closure element 50. The air expeller is open to the atmosphere by co-operation between the inner lip 215 of the piston 21 and the fluting 615 of the cylindrical surface 614.

When it is desired to actuate the device, the user presses on the pusher element 25, as with the above-described embodiments. During this initial stroke, the inner lip 215 of the piston leaves the fluting 615 so as to come to co-operate in airtight manner with the cylindrical surface 614, thereby closing the air chamber 22. At the same moment, the top edge 251 of the pusher element 25 comes into contact with the axial extension 216 of the piston 21, and the top axial end 610 of the first rod portion 61 comes into contact with the axial extension 43 of the retainer member 40. However, the top axial end 621 of the second rod portion 62 is still not in contact with the rounded surface 55 of the closure element 50. This can be seen in FIG. 20.

Figure 21:
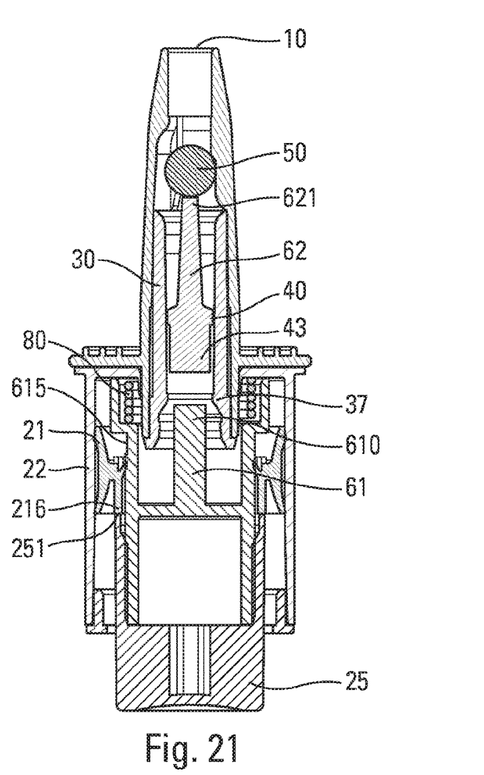

Continued actuation thus simultaneously moves the piston 21 in the air chamber, thereby compressing the air contained therein, and moves the retainer member 40 away from its position of closing the reservoir 30. When the second rod portion 62 contacts the closure element 50, said closure element is expelled mechanically from its closed position, so as to enable the composition to be expelled under the effect of the air compressed by the air expeller. The dispensing position is shown in FIG. 21. As can be seen in FIG. 21, the retainer member 40 may become detached from the first rod portion 61 while the composition is being expelled under the effect of the compressed air provided by the air expeller.

Figure 22:
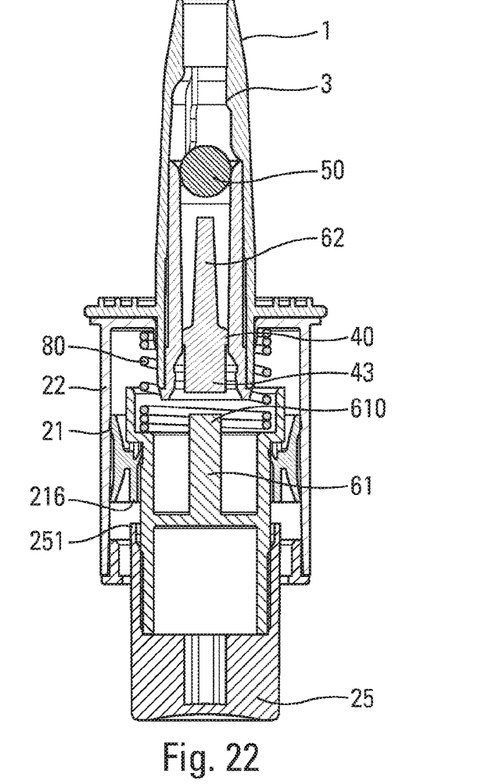
Figure 23:
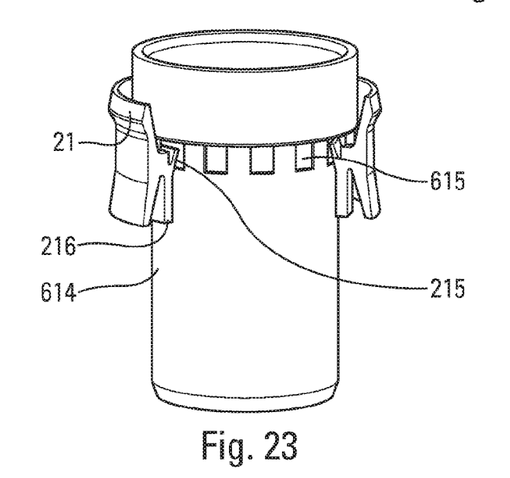
FIG. 23 is a diagrammatic perspective view of the air expeller of the device in FIGS. 19 to 22, in its rest position.

When the user relaxes the device, the spring 80 that was compressed during actuation, returns the first rod portion 61 towards its rest position. This creates suction that sucks the closure element 50 and the retainer member 40 back towards, or close to, their closure positions. This thus blocks the path for new suction so as to avoid soiling the air expeller while it returns automatically into its rest position, with the empty reservoir still assembled on the air expeller. However, the piston 21 remains in its dispensing position as a result of friction with the air chamber 22 and of the suction created in the reservoir 30, such that the cylindrical surface 614 slides over the inner lip 215 of the piston until said inner lip co-operates once again with the fluting 615. At this moment, the air chamber 22 is once again in communication with the surrounding air, and suction is no longer created by the return into the rest position. The piston 21 is thus also entrained towards its rest position. This makes it possible to close the reservoir after use.

Optionally, the unit formed by the dispenser head 1 and the empty reservoir 30 could be removed from the air expeller and replaced by a new unit that includes a full reservoir.

FIGS. 24 to 27 show a fourth embodiment. In this embodiment, the unit formed by the dispenser head 1 and the reservoir 30 is similar to the unit described above with reference to the third embodiment.

The piston 21 is once again separate from the first rod portion 61. The piston 21 slides in an air chamber 22 that is substantially similar to the air chamber of the first embodiment, namely with a larger-diameter portion at its bottom axial edge, so as to guarantee that the air chamber is put into communication with the surrounding air in the rest position. However, this is but one possible example.

A spring 80 is arranged between the radial flange 225 of the air chamber 22 and the piston 21, so as to return the piston 21 automatically into its rest position after actuation.

The piston 21 is secured to a hollow sleeve 217 that is provided at its top axial end with a retainer shoulder 2170. The bottom portion of the first rod portion 61 is suitable for sliding in said hollow sleeve 217. At its bottom axial end, it includes a radial projection 617 that co-operates with said retainer shoulder 2170 so as to retain said radial projection 617 of said first rod portion 61 inside said hollow sleeve 217. The top portion of said first rod portion includes said top axial end 610 that co-operates with the axial extension 43 of the retainer member 40 during actuation. The top portion also includes a plurality of axial tabs that form a hollow outer sleeve 618 that surrounds said top axial end 610, and that may possibly include snap-fastener means 619.

Figure 24:
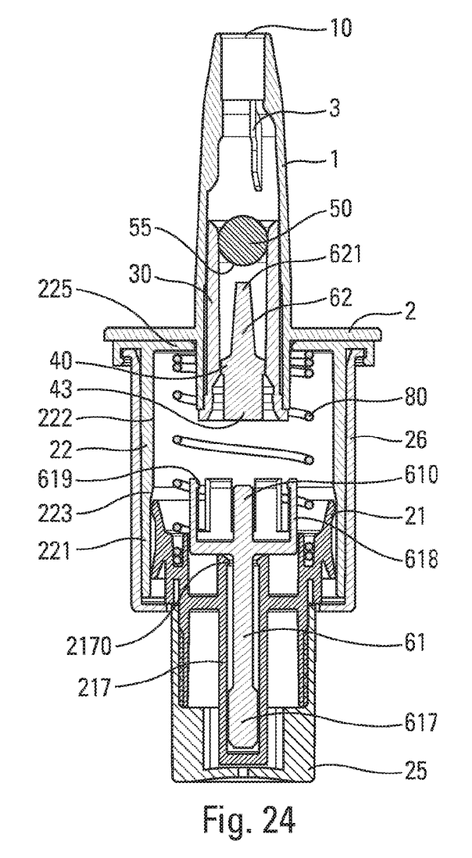
FIGS. 24 to 27 are diagrammatic section views of a fourth embodiment shown respectively in the rest position, during actuation, in the dispensing position, and during return of the air expeller towards its rest position.

In the rest position in FIG. 24, the air chamber 22 is open to the atmosphere and the reservoir 30 is closed, as described above.

Figure 25:
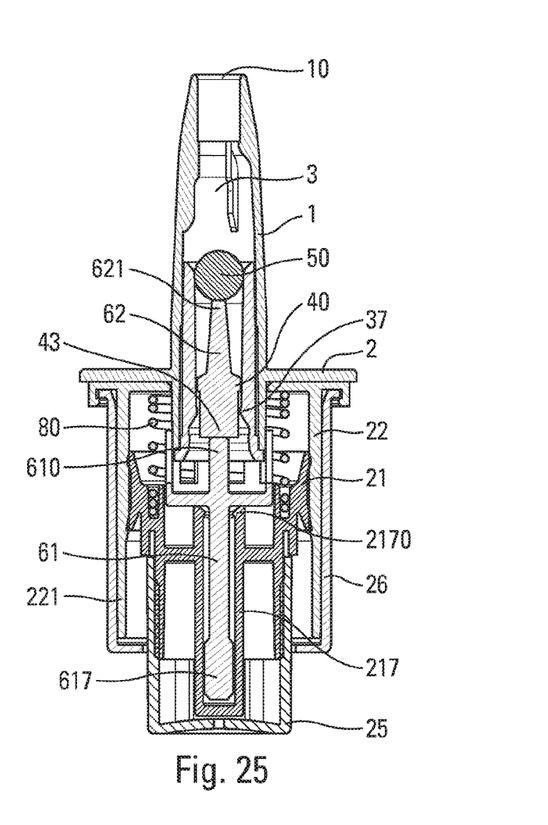
Figures 26, 27:
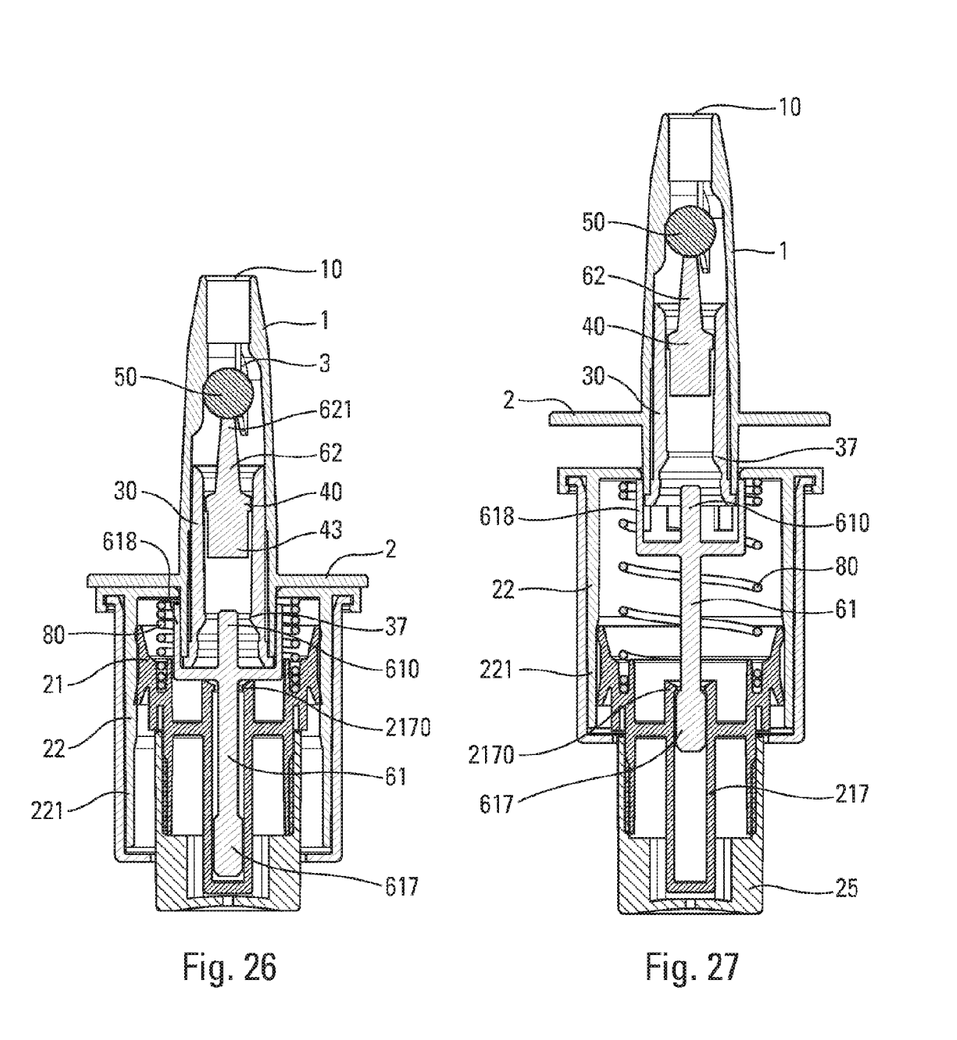
Figure 28:
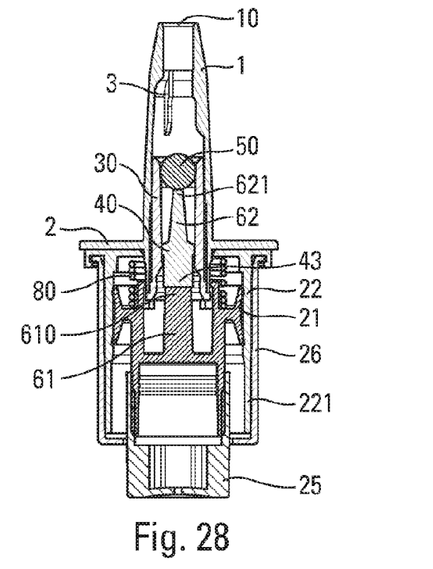
FIGS. 28 to 31 are diagrammatic section views of a fifth embodiment shown respectively during actuation, in the dispensing position, during return of the air expeller towards its rest position, and before putting a new full reservoir into place.
Figure 29:
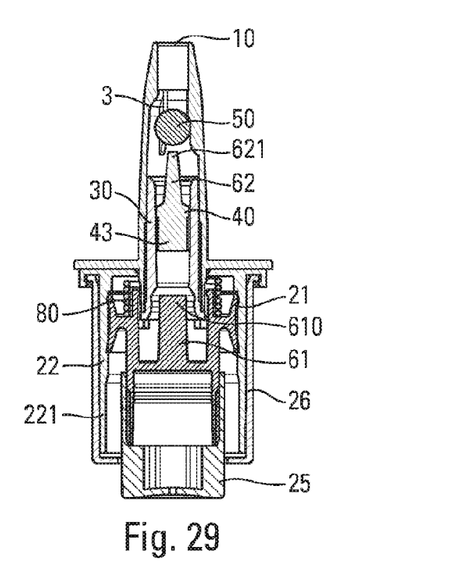
Figure 30:
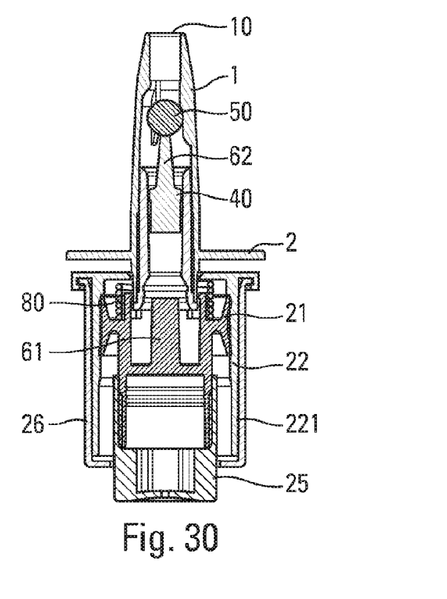

During actuation, the air chamber 22 closes, thereby enabling the piston 21 of the air expeller to compress the air contained in the air chamber 22 and to compress the spring 80. In parallel, the top axial end 610 of the first rod portion enters into contact with the retainer member 40 via its axial extension 43. The outer sleeve 618 becomes fitted around the bottom edge of the reservoir 30 and of the dispenser head 1, as can be seen in FIGS. 25 and 26. FIG. 26 shows the dispensing position in which the closure element 50 has been pushed by the second rod portion 62 away from its closed position, enabling the composition to be expelled through the dispenser opening by the flow of compressed air created by the air expeller.

When the user relaxes the device, the spring 80 returns the portion 21 towards its rest position. During this movement, the outer sleeve 618 of the first tab portion 61 remains jammed on the unit formed of the reservoir 30 and of the dispenser head 1. The first rod portion 61 is thus not returned towards its rest position, and it slides in the hollow sleeve 217, as can be seen in FIG. 27. The outer sleeve 618 thus blocks the path for new suction so as to avoid soiling the air expeller. When the empty reservoir is removed, the user unclips or unjams said first rod portion 61, which may then return towards its rest position, e.g. by gravity. Given that, in the rest position of the piston, there is no longer any suction since the air chamber 22 is in communication with the atmosphere, there is no risk of new suction while changing reservoir.

Figure 31:
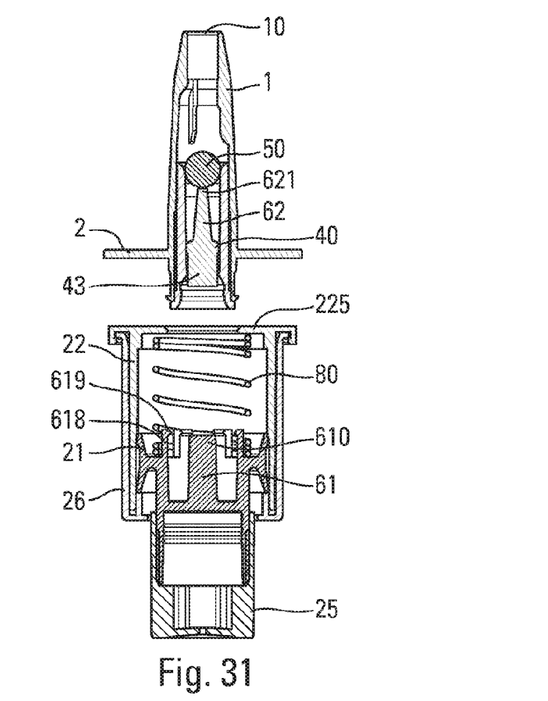

FIGS. 28 to 31 show a fifth embodiment. In this embodiment, the piston 21 is once again secured to the first rod portion 61, and it includes the same outer sleeve 618 as the outer sleeve described above with reference to FIGS. 24 to 27. During actuation, it is thus the piston 21 and the first rod portion 61 that become fitted around the reservoir and that are retained in this position after dispensing, when the user relaxes the actuation force. In this variant, the spring 80 remains compressed until the empty reservoir is removed. Snap-fastener means 619 on said axial tabs of the outer sleeve 618 are thus advantageous for guaranteeing a stable position despite the presence of the compressed spring. In particular, the snap-fastener means 619 may co-operate with an appropriate profile on the reservoir or on the dispenser head. When the user removes the empty reservoir, as can be seen in FIG. 31, the outer sleeve 618 is released, and the spring returns the air expeller into its rest position.

Figure 32:
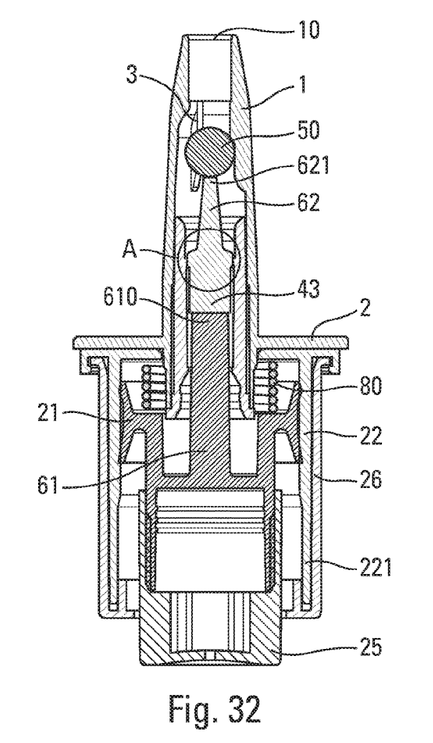
FIGS. 32 and 33 are diagrammatic section views of a sixth embodiment shown respectively in the dispensing position, and after return of the air expeller to its rest position.
Figure 32A:
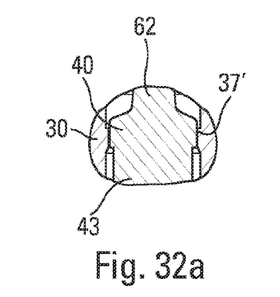
FIG. 32a is a view of a detail A of FIG. 32.
Figure 33:
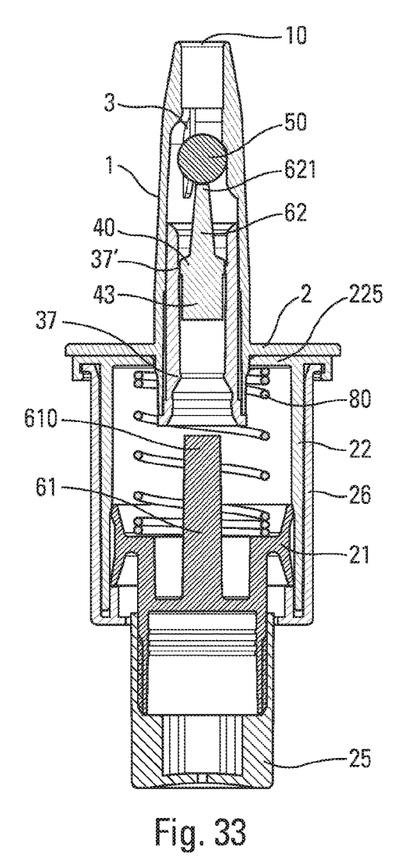

FIGS. 32 to 33 show a sixth embodiment. In this embodiment, the air expeller is similar to the air expeller of the above-described embodiment in FIGS. 28 to 31, with the first rod portion 61 secured to the piston 21. However, in this embodiment, there is no outer sleeve that comes to block the piston and the first rod portion on the reservoir in the dispensing position. When the user has terminated actuation, the spring 80 thus automatically returns the air expeller into its rest position, as can be seen in FIG. 33. In order to avoid new suction during this return, the reservoir 30 includes a second radial shoulder 37' that is offset axially upwards relative to the axial shoulder 37 that jams the retainer member in the closed position before actuation. The second radial shoulder 37' can be seen in particular in FIG. 32a. It makes it possible to jam the retainer member 40 in the dispensing position, and this avoids suction into the air expeller.

Although intended mainly for dispensing a powder composition, the present invention also applies to dispensing liquids.

The present invention is described above with reference to several embodiments, but naturally any modification could be applied thereto by a person skilled in the art, without going beyond the ambit of the present invention, as defined by the accompanying claims.

The invention claimed is:

1. A dispenser device for dispensing a fluid or powder composition, the dispenser device including: a dispenser outlet; an air expeller for generating a flow of air while the device is being actuated, said air expeller including a piston that slides in an air chamber between a rest position and a dispensing position, said air chamber including a cylindrical body in which said piston slides in airtight manner; and at least one reservoir that contains a single dose of composition, said reservoir including an air inlet that is connected to said air expeller, and a composition outlet that is connected to said dispenser outlet, said air inlet including a composition retainer member for retaining the composition in the reservoir until the composition is dispensed, and said composition outlet being closed by a closure element that is force fitted in the composition outlet of the reservoir; said device further including a mechanical opening system that co-operates with said closure element so as to expel said closure element mechanically from a closed position while the device is being actuated, said piston of said air expeller, when in the rest position, co-operating in non-airtight manner with said air chamber, in such a manner that said air chamber is in communication with the atmosphere in the rest position, wherein said piston includes an inner lip configured to cooperate with a cylindrical surface of a cylindrical member extending inside the cylindrical body, said cylindrical surface including fluting that co-operates in non-airtight manner with said inner lip of the piston in the rest position.

2. A device according to claim 1, wherein said cylindrical member is secured to a first rod portion that slides in said air chamber during actuation, said piston co-operating in airtight manner with said cylindrical body in any position, and co-operating in non-airtight manner with said cylindrical surface only in the rest position.

3. A device according to claim 1, wherein said reservoir is mounted in removable manner on said air expeller, such that after the device has been actuated, the empty reservoir may be removed from said air expeller and replaced by a new full reservoir, said air expeller being suitable for returning into its rest position so as to enable said new full reservoir to be actuated.

* * * * *